United States Patent
Ahn et al.

(10) Patent No.: US 8,969,069 B2
(45) Date of Patent: Mar. 3, 2015

(54) GLYCATED PROTEIN MEASUREMENT SENSOR AND PORTABLE GLYCATED PROTEIN MEASUREMENT APPARATUS INCLUDING SAME

(71) Applicants: NDD, Inc., Gumi-si (KR); IM Healthcare Co., Ltd., Wonju-si (KR); Fuzbien Technology Institute Inc., Rockville, MD (US)

(72) Inventors: Saeyoung Ahn, Seoul (KR); Steingrimur Stefansson, Rockville, MD (US)

(73) Assignees: NDD, Inc. (KR); IM Healthcare Co., Ltd. (KR); Fuzbien Technology Institute Inc., Rockville, MD (US)

( * ) Notice: Subject to any disclaimer, the term of this patent is extended or adjusted under 35 U.S.C. 154(b) by 0 days.

(21) Appl. No.: 14/345,269

(22) PCT Filed: Sep. 17, 2012

(86) PCT No.: PCT/KR2012/007417
§ 371 (c)(1),
(2) Date: Apr. 21, 2014

(87) PCT Pub. No.: WO2013/039362
PCT Pub. Date: Mar. 21, 2013

(65) Prior Publication Data
US 2014/0335629 A1    Nov. 13, 2014

(30) Foreign Application Priority Data

Sep. 15, 2011 (KR) .......... 10-2011-0093115
Sep. 14, 2012 (KR) .......... 10-2012-0102479

(51) Int. Cl.
*C12M 1/34* (2006.01)
*G01N 27/06* (2006.01)

(52) U.S. Cl.
CPC ............. *G01N 27/06* (2013.01); *Y10S 436/806* (2013.01); *Y10S 436/815* (2013.01)
USPC ............... 435/287.1; 422/82.01; 436/525; 436/806; 436/815; 204/403.01

(58) Field of Classification Search
None
See application file for complete search history.

(56) References Cited

U.S. PATENT DOCUMENTS 8,338,183 B2 *  12/2012  Nam et al. ............. 436/67
(Continued)

FOREIGN PATENT DOCUMENTS

KR    1020060133989    12/2006
(Continued)

OTHER PUBLICATIONS

International Search Report—PCT/KR2012/007417 dated Mar. 28, 2013.
Korean Office Action—Korean Application No. 10-2011-0093115, issued on Nov. 14, 2011.
(Continued)

*Primary Examiner* — Chris L Chin
(74) *Attorney, Agent, or Firm* — Cantor Colburn LLP (57) ABSTRACT

Disclosed are a glycated protein measurement sensor and a portable glycated protein measurement apparatus. The glycated protein measurement sensor includes: a sensing film (300) formed on a predetermined base material (100); and first and second unit sensors (10', 10") including a positive (+) electrode (400) and a negative (−) electrode (500) disposed facing each other at a predetermined distance on both ends of the sensing film (300). A ligand composition (600') including an aromatic boron acid combined with a first target material (700) as an effective component is disposed on the first sensing film (300) of the first unit sensor (10'). Also, a receptor (600") combined with the first or second target material (700) is disposed on the second sensing film (300) of the second unit sensor (10"). Here, the first target material (700) is a glycated protein (700'), and the second target material (700) is a protein (700").

13 Claims, 4 Drawing Sheets

(56) References Cited

U.S. PATENT DOCUMENTS

2009/0246801 A1* 10/2009 Smith .......................... 435/7.1
2009/0308744 A1* 12/2009 Nam et al. ............... 204/403.07
2010/0270177 A1 10/2010 Fujiwara et al.

FOREIGN PATENT DOCUMENTS

| | | |
|---|---|---|
| KR | 100907474 | 7/2009 |
| KR | 100945571 | 2/2010 |
| KR | 101019348 | 2/2011 |
| WO | WO 2008016193 A1 * | 2/2008 |

OTHER PUBLICATIONS

Korean Office Action—Korean Application No. 10-2012-0102479 issued on Mar. 1, 2013.
Korean Office Action—Korean Application No. 10-2012-0102479 issued on Mar. 27, 2013, and Debasmita Das et al., A Glucose Sensor Based on an Aminophenyl Boronic Acid Bonded Conducting Polymer, Electroanalysis, 2011, pp. 2036-2041.
Debasmita Das et al., A Glucose Sensor Based on an Aminophenyl Boronic Acid Bonded Conducting Polymer, Electroanalysis, 2011, pp. 2036-2041.

* cited by examiner

GLYCATED PROTEIN MEASUREMENT SENSOR AND PORTABLE GLYCATED PROTEIN MEASUREMENT APPARATUS INCLUDING SAME

FIELD OF THE INVENTION

The present invention relates to a glycated protein measurement sensor and a portable glycated protein measurement apparatus including the same. More particularly, the present invention relates to a glycated protein measurement sensor capable of simply measuring glycated protein level by merely bringing saliva into contact with the measurement sensor without blood collection, and a portable glycated protein measurement apparatus including the same.

BACKGROUND

Nanoscale-sized materials have recently been in the spotlight due to their distinctive electrical, optical, and mechanical characteristics. Researches so far conducted on nanostructures show that, on account of new phenomena such as quantum size effects, they are applicable for new optical devices in the future. In particular, such nanostructures can be used not only for single electron transistor devices but also for various chemical sensors and biosensors, and thus are receiving more attention.

Detection of target materials using a biosensor including a nanostructure is implemented in such a manner that a receptor fixed on a surface of the nanostructure is allowed to adsorb target materials (chemical markers, biomolecules, or disease-specific markers) on the surface of the nanostructure, and the adsorbed target materials cause a change in the conductivity of the nanostructure.

This change in the conductivity of the nanostructure may be used to detect target materials in a human body, for example, plasma proteins in a diabetic patient.

Diabetes is a kind of metabolic disease in which the amount of insulin produced by pancreas is insufficient or insulin does not properly function. Diabetic patients should undergo diet therapy, exercise therapy, drug therapy, and the like in order to manage their blood sugar levels. Therefore, the diabetic patients are required to regularly measure the sugar levels every day to get the above therapies.

According to a conventional method of determining a blood sugar level, a small quantity of blood sample obtained by pricking a finger of a patient is put in a chemically treated sensor to measure the blood sugar level. Such a method has been disclosed in Korean Laid-open Patent Publication No. 2010-0086039 or the like.

The above conventional method of determining a blood sugar level entails frequent blood collection, which inflicts pain on patients and causes problems such as bacterial infection and the like. Moreover, since it takes some time to put a blood sample in a chemically treated sensor, an error may occur in the measurement of the blood sugar level. Therefore, there have been continuous demands for developing methods that may more accurately measure sugar levels of diabetic patients in real time without blood collection.

SUMMARY OF THE INVENTION

Therefore, the present invention has been contrived to solve the above-mentioned problems of the prior art, and one object of the invention is to provide a glycated protein measurement sensor capable of simply measuring glycated protein level by merely bringing saliva into contact with the measurement sensor without blood collection, and a portable glycated protein measurement apparatus including the same.

Another object of the invention is to provide a glycated protein measurement sensor capable of easily measuring glycated protein level in real time and a portable glycated protein measurement apparatus including the same.

Yet another object of the invention is to provide a glycated protein measurement sensor of which measurement precision is improved and manufacturing process is simplified, and a portable glycated protein measurement apparatus including the same.

In accordance with one aspect of the invention to achieve the objects as described above, there is provided a glycated protein measurement sensor, comprising a ligand composite containing aromatic boronic acid as an active ingredient.

In accordance with another aspect of the invention to achieve the above objects, there is provided a glycated protein measurement sensor, comprising: first and second unit sensors, each comprising a sensing film being formed on a substrate; and positive (+) and negative (−) electrodes being formed at both ends of the sensing film facing each other at a predetermined interval, wherein a ligand composite is disposed on a first sensing film of the first unit sensor, the ligand composite containing, as an active ingredient, aromatic boronic acid binding to a first target material, and a receptor is disposed on a second sensing film of the second unit sensor, the receptor binding to the first target material or a second target material, and wherein the first target material is glycated protein and the second target material is protein.

Here, when saliva is in contact with at least a portion of the first sensing film of the first unit sensor, the change in current flowing in the first sensing film may be measured, wherein the change is induced by the connection of the first sensing film with the glycated protein in the saliva via the ligand composite containing the aromatic boronic acid as the active ingredient. Meanwhile, when saliva is in contact with at least a portion of the second sensing film of the second unit sensor, the change in current flowing in the second sensing film may be measured, wherein the change is induced by the connection of the second sensing film with the glycated protein or the protein in the saliva via the receptor.

A material for the substrate may include any one of silicon, glass, plastic and polymer, and a surface of the substrate may have a hydrophobic property.

Materials for the first and second sensing films are the same, and may include any one of carbon nanotubes and graphene.

Materials for the positive (+) and negative (−) electrodes may include gold.

The negative (−) electrode of the first unit sensor and the negative (−) electrode of the second unit sensor may be the same and connected with a ground.

The aromatic boronic acid may include any one of phenyl boronic acid, naphthalene boronic acid, phenanthrene boronic acid, and pyrene boronic acid.

The receptor may include a thiol group.

The glycated protein may include any one of glycated human serum albumin (gHSA), glycated IgG and glycated IgM.

The protein may include any one of human serum albumin (HSA), IgG and IgM.

The glycated protein measurement sensor may further comprise a gate electrode as another negative (−) electrode when the positive (+) electrode is a source electrode and the negative (−) electrode is a drain electrode.

In accordance with yet another aspect of the invention to achieve the objects as described above, there is provided a portable glycated protein measurement apparatus, comprising the glycated protein measurement sensor; a sensor body covering the glycated protein measurement sensor and forming an external appearance thereof; and a terminal part being formed at one end of the glycated protein measurement sensor.

In accordance with still another aspect of the invention to achieve the objects, there is provided a method of measuring glycated protein level using the glycated protein measurement sensor.

According to the invention, glycated protein level can be simply measured by merely bringing saliva into contact with a measurement apparatus without blood collection.

Further, according to the invention, glycated protein level can be easily measured in real time.

Furthermore, according to the invention, glycated protein level can be accurately measured with minimum error, and manufacturing process can be simplified.

DETAILED DESCRIPTION OF THE PREFERRED EMBODIMENTS

In the following detailed description of the invention, references are made to the accompanying drawings that show, by way of illustration, specific embodiments in which the invention may be practiced. These embodiments are described in sufficient detail to enable those skilled in the art to practice the invention. It is to be understood that the various embodiments of the invention, although different from each other, are not necessarily mutually exclusive. For example, specific shapes, structures, or characteristics described herein may be implemented as modified from one embodiment to another without departing from the spirit and the scope of the invention. Furthermore, it shall be understood that the locations or arrangements of individual elements within each embodiment may be also modified without departing from the spirit and the scope of the invention. Therefore, the following detailed description is not to be taken in a limiting sense, and the scope of the invention is to be taken as encompassing the scope of the appended claims and all equivalents thereof, as long as properly described. In the drawings, like reference numerals refer to the same or similar functions throughout the several views, and certain features such as length, area, thickness and shape may be exaggerated for convenience.

Hereinafter, various preferred embodiments of the present invention will be described in detail with reference to the accompanying drawings to enable those skilled in the art to easily implement the invention.

Configuration of Glycated Protein Measurement Sensor

Figure 1:
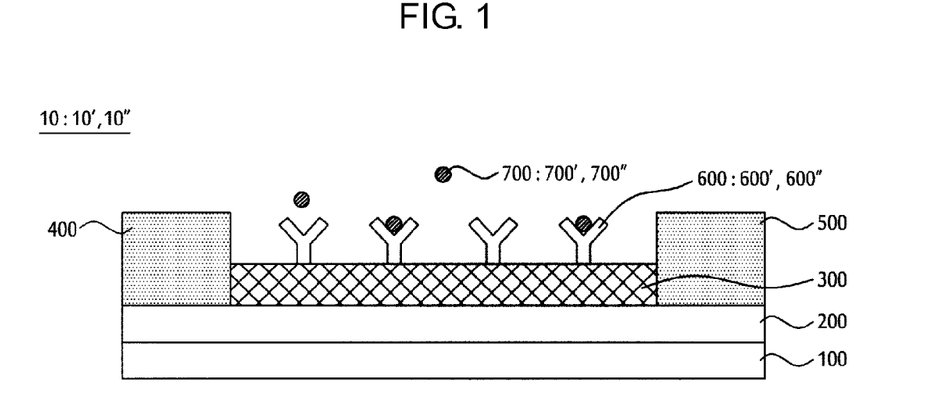
FIG. 1 shows the configuration of a glycated protein measurement unit sensor according to one embodiment of the invention.

FIG. 1 shows the configuration of a glycated protein measurement unit sensor according to one embodiment of the invention.

Referring to FIG. 1, a unit sensor 10 may include a substrate 100, an oxide layer 200, a sensing film 300, a first electrode 400 and a second electrode 500.

Figure 2:
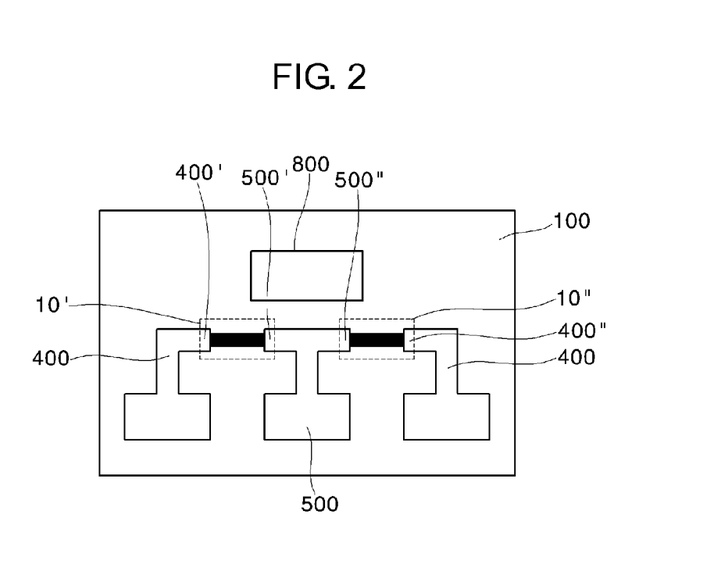
FIG. 2 shows the configuration of a glycated protein measurement sensor according to one embodiment of the invention.

The substrate 100 may function as a glycated protein measurement substrate, and a portion of a common silicon wafer may be used for the substrate 100. However, it is not necessarily limited thereto, and glass, plastic, or polymer may be used as a material for the substrate 100 in some cases. Meanwhile, FIG. 1 shows that the size of the substrate 100 is restricted to the unit sensor 10. However, as shown in FIG. 2, the components of the unit sensor 10, i.e., the oxide layer 200, the sensing film 300, the positive (+) electrode 400, the negative (−) electrode 500 and the like may be included on a portion of the substrate 100 (i.e., the portable glycated protein measurement substrate). In other words, at least two unit sensors 10 may be formed on the portable glycated protein measurement substrate 100.

The oxide layer 200 may be formed on the substrate 100, and may contain silica ($SiO_2$). The oxide layer 200 may serve as a gate insulating layer. The oxide layer 200 may be formed by thermal oxidation, physical vapor deposition (PVD), chemical vapor deposition (CVD) or the like. However, without being restricted thereto, the oxide layer 200 may be formed by any known thin film forming methods without limitation.

The sensing film 300 may be formed on the oxide layer 200 and serve as a semiconductor, i.e., serve to change the amount of current flowing between a pair of the positive (+) electrode 400 and the negative (−) electrode 500 when a target material 700 such as glycated protein 700' or protein 700" is adsorbed on a surface of the sensing film 300.

In particular, any one of carbon nanotubes (CNTs) and graphene may be used as a material constituting the sensing film 300. Carbon nanotubes used for the sensing film 300 may be in the form of a single wall, a double wall, a multi-wall or the like, and in some cases, in the form of a rope. Graphene is in the form of a single layer of graphite, which is a thin carbon film with the thickness of a single atom. Graphene has excellent electrical and thermal conductivity as well as high strength, and the chemical properties thereof are similar to those of the carbon nanotubes.

Carbon nanotubes generally exhibit a strong hydrophobic property. Therefore, an upper surface of the oxide layer 200 may be modified to have a hydrophobic property so that the sensing film 300 made of carbon nanotubes may be easily formed on the oxide layer 200.

The positive (+) electrode 400 and the negative (−) electrode 500 may be disposed at both ends of the sensing film 300 facing each other at a predetermined interval. The materials for the positive (+) electrode 400 and the negative (−) electrode 500 may preferably be gold (Au). Meanwhile, the positive (+) electrode 400 may function as a separate electrode and the negative (−) electrode may function as a common electrode, as will be described below.

FIG. 2 shows the configuration of a glycated protein measurement sensor according to one embodiment of the invention.

Referring to FIG. 2, the glycated protein measurement sensor of the invention may include at least two unit sensors 10. Hereinafter, the glycated protein measurement sensor will be described on the assumption that it includes two unit sensors 10, i.e., a first unit sensor 10' and a second unit sensor 10". The first unit sensor 10' and the second unit sensor 10" have substantially the same components in terms of a substrate 100, an oxide layer 200, a sensing film 300, a positive (+) electrode 400 and a negative (−) electrode 500.

Figure 3:
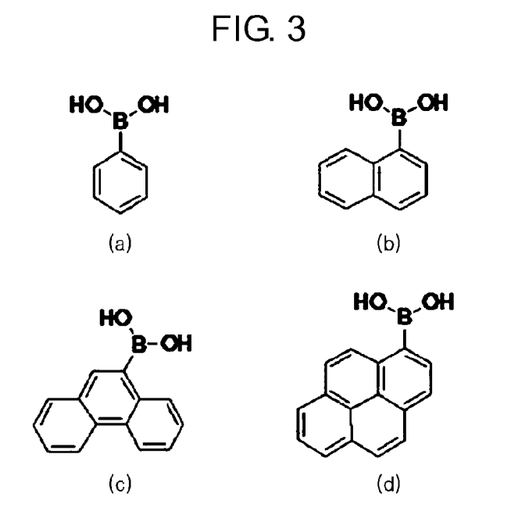
FIG. 3 shows the structure of a ligand composite according to one embodiment of the invention.

In the first unit sensor 10', a ligand composite 600' is disposed on a first sensing film 300. Herein, the term "disposing" may refer to uniformly placing a predetermined material on the sensing film 300 through coating, adsorption, deposition or the like. The ligand composite 600' may serve to bind to glycated protein 700', which is a first target material 700, so that the glycated protein 700' may adhere onto the sensing film 300. The ligand composite 600' may contain aromatic boronic acid as an active ingredient, and may particularly contain any one of phenyl boronic acid, naphthalene boronic acid, phenanthrene boronic acid, and pyrene boronic acid. In FIG. 3, (a) represents phenyl boronic acid; (b) naphthalene-1 boronic acid; (c) 9-phenanthrene boronic acid; and (d) pyrene-1 boronic acid.

The glycated protein 700' may be any one of glycated human serum albumin (gHSA), glycated IgG and glycated IgM.

In the second unit sensor 10", a receptor 600" is disposed on a second sensing film 300. The receptor 600" may serve to bind to glycated protein 700' or protein 700", which is a first or second target material 700, so that the glycated protein 700' or the protein 700" may adhere onto the sensing film 300. The receptor 600" may be a material selected from a group consisting of an enzyme substrate, a ligand, amino acid, peptide, protein, nucleic acid, lipid, and carbohydrate, and may preferably be thyroxine.

The protein 700" may be any one of human serum albumin (HSA), IgG and IgM.

The above unit sensor 10 has a structure similar to that of a metal oxide semiconductor field effect transistor (MOSFET), wherein the sensing film 300 may serve as a channel, the positive (+) electrode 400 as a source electrode, and the negative (−) electrode 500 as a drain electrode. Meanwhile, a gate electrode 800 as another negative (−) electrode may be formed in the portable glycated protein measurement substrate 100. In particular, when carbon nanotubes having semiconductor characteristics are employed as a material constituting the sensing film 300, the unit sensor 10 may serve as a carbon nanotube field effect transistor (CNT-FET).

The glycated protein 700' present in saliva may bind to the ligand composite 600' of the first unit sensor 10' to adhere onto the first sensing film 300, thereby changing the level of current flowing in the first unit sensor 10'. That is, the first sensing film 300 may be connected with the glycated protein 700' via the ligand composite 600' to induce the change in current in the first sensing film 300. In addition, the glycated protein 700' or the protein 700" present in saliva may bind to the receptor 600" of the second unit sensor 10" to adhere onto the second sensing film 300, thereby changing the level of current flowing in the second unit sensor 10". That is, the second sensing film 300 may be connected with the glycated protein 700' or the protein 700" via the receptor 600" to induce the change in current in the second sensing film 300. Therefore, the amount of current flowing within the first unit sensor 10' or the second unit sensor 10" may be changed depending on the amount of glycated protein 700' or protein 700" contained in a predetermined detection solution (i.e., saliva).

Meanwhile, FIG. 2 shows that two unit sensors 10 are disposed in the glycated protein measurement sensor. However, without being limited thereto, the number of unit sensors 10 may be increased according to the purpose of implementing the present invention. For example, if four unit sensors 10 are disposed, one more first unit sensor 10' and one more second unit sensor 10" may respectively be added.

The positive (+) electrode 400 may serve as a source electrode as a separate electrode 400 in the glycated protein measurement sensor in which at least two unit sensors 10 are disposed. In addition, the positive (+) electrode 400 is not limited to the size, shape and the like of the electrode shown in FIG. 2, and may be variously modified as long as it may serve as the source electrode.

Further, referring again to FIG. 2, the negative (−) electrode 500 may function as a common electrode 500 in the glycated protein measurement sensor in which at least two unit sensors 10 are disposed. For example, it may function as the same electrode shared by the first unit sensor 10' and the second unit sensor 10". The common electrode 500 is connected with the plurality of unit sensors 10 so that it may serve as a drain electrode by receiving a ground voltage from voltage applying means (not shown).

Meanwhile, the voltage applying means may apply a plus voltage while being in contact with the positive (+) electrode 400. In addition, the voltage applying means may apply a ground voltage while being in contact with the negative (−) electrode 500. When the voltages are applied from the voltage applying means to the respective electrodes as above, the change in current in each unit sensor may be measured through a terminal part 920 (see FIG. 6) connected with the positive (+) electrode 400 and the negative (−) electrode 500.

In particular, by measuring the change in the current flowing in the first unit sensor 10' and the change in the current flowing in the second unit sensor 10", the glycated protein level detected in the first unit sensor 10' and the total protein level detected in the second unit sensor 10" (glycated protein level plus protein level) may be compared with each other. That is, whether a subject is a diabetic patient or not may be determined by measuring the value of gHSA/total HSA (gHSA+HSA), i.e., the amount of glycated protein that has been changed from the total protein present in the saliva of a diabetic patient. For example, if the value is measured to be 14% or higher, it means that 14% or more of the total protein has been glycated, and thus the subject may be determined to be a diabetic patient.

EXAMPLE

In the following example, a glycated protein measurement sensor (CNT-FET) according to the present invention was manufactured, and then the change in current induced by the binding of glycated protein and carbon nanotubes was recognized.

Materials used for manufacturing the glycated protein measurement sensor of the invention were as follows.

Single-wall CNTs having a diameter of 0.7 nm to 1.4 nm and a length of 20 nm to 80 nm were used. The glycated protein measurement sensor was manufactured using standard photolithography and lift-off processes. Pyrene boronic acid, 9-phenanthrene boronic acid, naphthalene-1 boronic acid, or phenyl boronic acid was used as aromatic boronic acid. In addition, sorbitol, dimethyl formamide (DMF), ethanol, gHSA (containing 1-5 moles of fructosamine per mole of albumin), and MOPS were prepared.

The manufacture of the glycated protein measurement sensor of the invention and the measurement of gHSA were performed as follows.

Aromatic boronic acid was dissolved in DMF. The optimum coating concentration of the aromatic boronic acid was determined by performing a series of dilutions in the DMF and then applying them to the CNT-FET. To prevent evaporation, the DMF mixture liquid in which 4 ml of the aromatic boronic acid was dissolved in a sealed container was incubated in the CNT-FET at room temperature for 30 minutes. After the incubation, the CNT-FET was washed with ethanol and dried in the air at room temperature for 1 hour. The reference impedance value of the CNT-FET was obtained by adding 4 ml of 0.1 M MOPS (pH 7.5) and 5 mM of $MgCl_2$ (a binding buffer) to the CNT-FET for 30 seconds, then adding 4 μl of gHSA in the same buffer to the CNT-FET, and further measuring the change in the impedance value for 2 minutes. The impedance value for the measurement of gHSA was normalized to a corresponding buffer reference value. Electrical properties of target materials binding to the CNT-FET were measured using a low-current measurement system that allows electrical contact with the source and drain electrodes of the CNT-FET. 100 mV of source/drain bias was maintained during the measurement of the electric signal, wherein the pulse width was 1 second.

Figure 4:
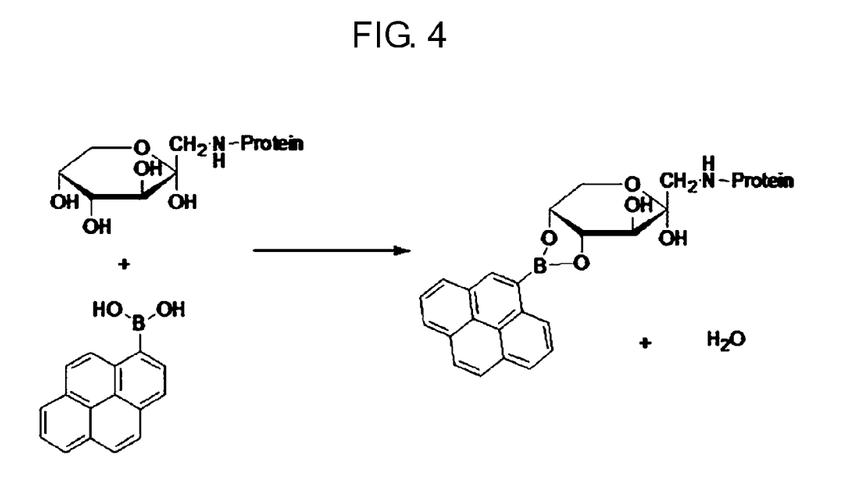
FIG. 4 shows the binding of a ligand composite and glycated protein according to one embodiment of the invention.

FIG. 4 shows the binding of a ligand composite and glycated protein according to one embodiment of the invention.

Referring to FIG. 4, the binding of a ligand composite 600' disposed on the first sensing film 300 of the first unit sensor 10' and glycated protein 700' can be seen.

An N-linked fructosamine-protein adduct, which is an initial product of a glycation procedure, has 1,2-cis-diol capable of forming a covalent ester bond with boronic acid. The boronic acid is of a planar type, and thus may form a bond only with planar cis-diol. Due to the formation of the stereospecific bond, immobilized amino-phenyl boronic acid may be used as a ligand composite 600' having an affinity for the glycated protein 700', which is a target material 700 of the first sensor 10.

Figure 5:
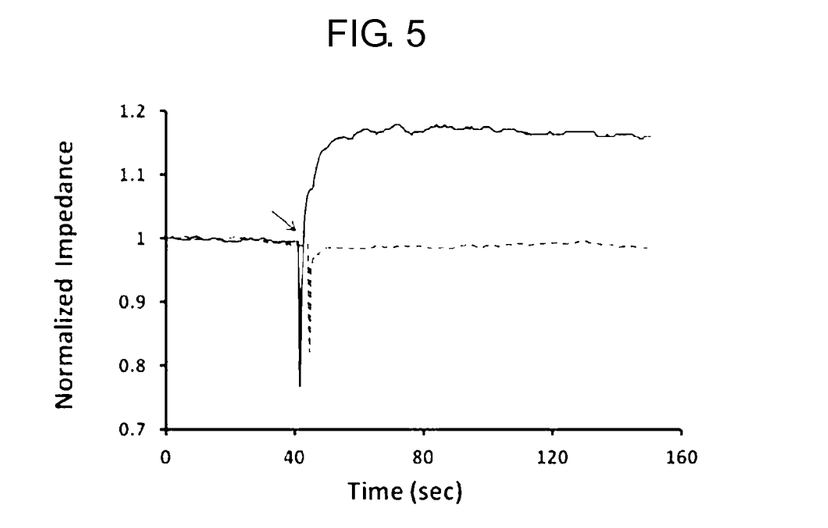
FIG. 5 shows the binding of aromatic boronic acid and glycated human serum albumin (gHSA) according to one embodiment of the invention.

FIG. 5 shows the binding of aromatic boronic acid and glycated human serum albumin (gHSA) according to one embodiment of the invention.

Referring to FIG. 5, when a detection solution containing a target material was applied (indicated by an arrow in FIG. 5), a significant change in impedance was recognized in the CNT-FET coated with pyrene-1 boronic acid (bold solid line) as compared to the non-coated CNT-FET (broken line). Accordingly, it can be seen that gHSA may adhere onto the CNT-FET in which aromatic boronic acid is disposed, so that the amount of current flowing within the CNT-FET may be changed.

Structure of Portable Glycated Protein Measurement Apparatus

Figure 6:
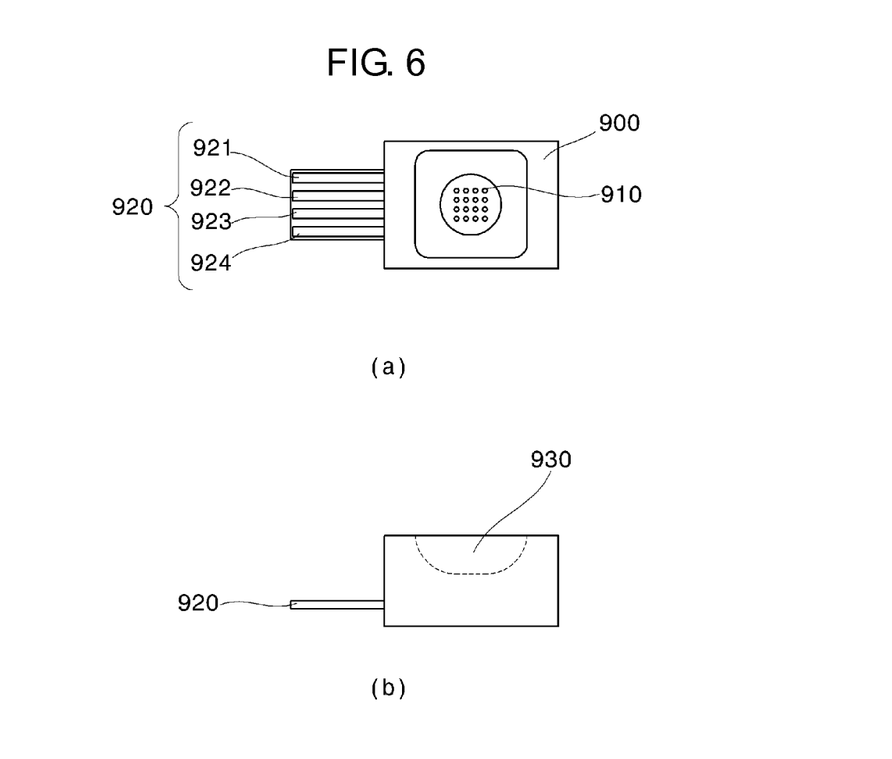
FIG. 6 shows a portable glycated protein measurement apparatus according to one embodiment of the invention.

FIG. 6 shows a portable glycated protein measurement apparatus according to one embodiment of the invention. In FIG. 6, (a) and (b) show top and side views of the portable glycated protein measurement apparatus, respectively.

Referring to FIG. 6, the portable glycated protein measurement apparatus according to one embodiment of the invention comprises a sensor body 900 and a terminal part 920.

The sensor body 900 may cover a potable glycated protein measurement substrate 100 or a glycated protein measurement sensor to protect the portable glycated protein measurement apparatus from external detection solutions or impact, and may constitute an external appearance of the portable glycated protein measurement apparatus. A material for the sensor body 900 is preferably plastic. However, any other material may be used as long as it may cover the glycated protein measurement sensor and constitute the external appearance.

The sensor body 900 may be provided with a plurality of holes 910 for passing saliva therethrough. Saliva may pass through the plurality of holes 910 to be in contact with the glycated protein measurement sensor within the sensor body 900.

Preferably, the sensor body 900 may be provided with a groove 930 for containing saliva. By means of the groove 930, a user may spit saliva in the groove 930 or easily transfer saliva having been separated from within the body, so as to measure glycated protein level.

Meanwhile, the portable glycated protein measurement apparatus may further comprise a sensor cover member (not shown) covering a unit sensor 10. A material for the sensor cover member may include plastic. A plurality of fine holes are formed in the sensor cover member, so that only target materials 700 present in a detection solution (e.g., glycated protein 700' and protein 700" present in saliva) may pass through the fine holes and bind to a ligand composite 600' and a receptor 600".

The terminal part 920 may be formed to connect with the glycated protein measurement sensor 10 and protrude outwardly from the sensor body 900. Wirings 921, 922, 923, and 924 of the terminal part 920 are respectively connected with a positive (+) electrode 400 connected to a first unit sensor 10', a positive (+) electrode 400 connected to a second unit sensor 10", a negative (−) electrode 500, and a gate electrode 800. Naturally, the number of wirings may be changed as the number of unit sensors 10 increases.

Figure 7:
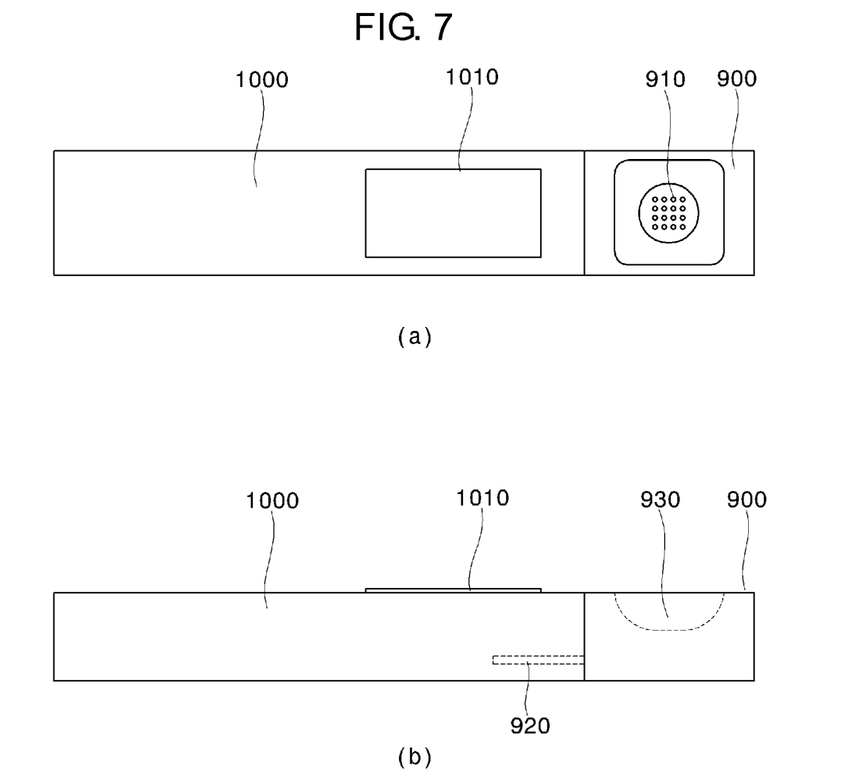
FIG. 7 shows the configuration in which a reader unit is connected with a portable glycated protein measurement apparatus according to one embodiment of the invention.

FIG. 7 shows the configuration in which a reader unit is connected with a portable glycated protein measurement apparatus according to one embodiment of the invention.

Referring to FIG. 7, the portable glycated protein measurement apparatus of the invention may further comprise a reader unit 1000. The reader unit 1000 may be attached to and detached from the sensor body 900, and may be provided with a terminal hole (not shown) into which the terminal part 920 may be inserted. The terminal part 920 is inserted into the reader unit 1000 to transmit a current signal related to glycated protein level and protein level to a control unit (not shown) of the reader unit 1000, so that the reader unit 1000 may analyze the glycated protein level and the protein level and calculate the value of gHSA/total HSA (gHSA+HSA). The value of gHSA/total HSA (gHSA+HSA) may be displayed through a display unit 1010 provided in the reader unit 1000.

Meanwhile, without being limited to the reader unit 1000, other terminal units such as a computer and a smart phone may be connected with the terminal part 920 to analyze the current signal and measure the glycated protein level. The portable glycated protein measurement apparatus of the present invention may be inexpensively manufactured in the size of a swab or a thermometer to enable simple and one-off measurement of the glycated protein level.

The present invention has an advantage in that glycated protein level may be easily measured in real time by merely bringing saliva into contact with a glycated protein measurement sensor including a ligand composite binding to glycated protein, with no need to conduct a blood collection procedure. Further, the present invention has another advantage in that the distance between CNTs and glycated protein (which is a target material) is relatively short, thereby improving the measurement precision and simplifying the manufacturing process.

Although the present invention has been illustrated and described as above in connection with the preferred embodiments, the invention is not limited to the above embodiments, and various modifications and changes may be made by those skilled in the art without departing from the spirit and scope of the invention. Such modifications and changes should be considered to fall within the scope of the invention and the appended claims.

What is claimed is:

1. A glycated protein measurement sensor, comprising:
   first and second unit sensors, each comprising:
   a sensing film being formed on a substrate; and
   positive (+) and negative (−) electrodes being formed at both ends of the sensing film facing each other at a predetermined interval,
   wherein a ligand composite is disposed on a first sensing film of the first unit sensor, the ligand composite containing, as an active ingredient, aromatic boronic acid binding to a first target material, and a receptor is disposed on a second sensing film of the second unit sensor, the receptor binding to the first target material and a second target material,
   wherein the first and second sensing films are identically configured to include any one of carbon nanotubes and graphene,
   wherein the first target material is glycated human serum albumin (gHSA) and the second target material is human serum albumin (HSA),
   wherein when saliva is in contact with at least a portion of the first sensing film of the first unit sensor, the change in current flowing in the first sensing film is measured, the change being induced by the connection of the first sensing film with the gHSA in the saliva via the ligand composite containing the aromatic boronic acid as the active ingredient, and
   wherein when saliva is in contact with at least a portion of the second sensing film of the second unit sensor, the change in current flowing in the second sensing film is measured, the change being induced by the connection of the second sensing film with the gHSA and HSA in the saliva via the receptor.

2. The glycated protein measurement sensor of claim 1, wherein a material for the substrate includes any one of silicon, glass, plastic and polymer, and a surface of the substrate has a hydrophobic property.

3. The glycated protein measurement sensor of claim 1, wherein materials for the positive (+) and negative (−) electrodes include gold.

4. The glycated protein measurement sensor of claim 1, wherein the negative (−) electrode of the first unit sensor and the negative (−) electrode of the second unit sensor are the same and connected with a ground.

5. The glycated protein measurement sensor of claim 1, wherein the aromatic boronic acid includes any one of phenyl boronic acid, naphthalene boronic acid, phenanthrene boronic acid, and pyrene boronic acid.

6. The glycated protein measurement sensor of claim 1, wherein the receptor is selected from a group consisting of an enzyme substrate, a ligand, amino acid, peptide, protein, nucleic acid, lipid, and carbohydrate.

7. The glycated protein measurement sensor of claim 1, further comprising a gate electrode as another negative (−) electrode when the positive (+) electrode is a source electrode and the negative (−) electrode is a drain electrode.

8. A portable glycated protein measurement apparatus, comprising:
   the glycated protein measurement sensor of claim 1;
   a sensor body covering the glycated protein measurement sensor and forming an external appearance thereof; and
   a terminal part being formed at one end of the glycated protein measurement sensor.

9. The apparatus of claim 8, wherein a groove for containing saliva is formed in the sensor body.

10. The apparatus of claim 9, wherein a plurality of holes for passing saliva therethrough are formed in the sensor body.

11. The apparatus of claim 8, further comprising a reader unit to analyze a signal transmitted from the terminal part, the reader unit being attached to and detached from the sensor body.

12. The apparatus of claim 11, wherein the reader unit comprises a display unit to display measured level of glycated protein.

13. The apparatus of claim 8, further comprising a sensor cover member covering the glycated protein measurement sensor, wherein a material for the sensor cover member includes plastic, and fine holes for passing a target material therethrough are formed in the sensor cover member.

* * * * *